United States Patent [19]

Magnussen, Jr.

[11] Patent Number: 4,820,129

[45] Date of Patent: Apr. 11, 1989

[54] PRESSURE MEASUREMENT IN FLUID PUMP SYSTEMS

[75] Inventor: Haakon T. Magnussen, Jr., Pinole, Calif.

[73] Assignee: Altex Scientific, Inc., Calif.

[21] Appl. No.: 386,453

[22] Filed: Jun. 8, 1982

[51] Int. Cl.⁴ .................... F04B 49/06; F04B 49/00
[52] U.S. Cl. ............................. 417/18; 210/101
[58] Field of Search ............... 210/101; 417/1, 53, 417/18, 22

[56] References Cited

U.S. PATENT DOCUMENTS

| | | | |
|---|---|---|---|
| 3,847,507 | 11/1974 | Sakiyama | 417/22 |
| 3,917,531 | 11/1975 | Magnusson | 210/101 |
| 4,221,543 | 9/1980 | Cosontino | 417/22 |
| 4,225,290 | 9/1980 | Allington | 417/18 |
| 4,233,156 | 11/1980 | Tsukada | 210/101 |
| 4,255,088 | 3/1981 | Newton | 417/1 |
| 4,326,837 | 4/1982 | Gilson | 417/22 |
| 4,352,636 | 10/1982 | Patterson | 417/22 |
| 4,359,312 | 11/1982 | Funke | 417/539 |
| 4,420,393 | 12/1983 | Smith | 210/101 |
| 4,448,692 | 5/1984 | Nakamoto | 210/101 |

Primary Examiner—William L. Freeh
Attorney, Agent, or Firm—William H. May; Paul R. Harder

[57] ABSTRACT

A fluid pump for use in high performance liquid chromatography having a piston movable in a chamber for drawing fluid into, pressurizing, and delivering the pressurized fluid from the chamber. A pressure transducer in the chamber derives a pressure output signal indicative of chamber pressure. Means is provided for correcting offset errors in the pressure output signal.

3 Claims, 3 Drawing Sheets

PRESSURE MEASUREMENT IN FLUID PUMP SYSTEMS

BACKGROUND OF THE INVENTION

1. Field of the Invention

The present invention relates to pressure measurement in fluid pumping systems and, more particularly, to the correction of pressure offset errors in such systems.

2. Description of the Prior Art

U.S. Pat. Nos. 4,131,393 and 4,190,375 describe fluid pump mechanisms for high-performance liquid chromatography (HPLC). In HPLC systems, a fluid sample mixture carried in a solvent matrix is pumped at high pressure through a densely packed separation column. The column separates the sample into individual sample fractions which exit the column one after another. The separated fractions flow in succession through a flow cell detector, such as a spectrophotometer, which performs quantitative and/or qualitative measurements of each fraction.

In a prior HPLC pump mechanism, system pressure is monitored with a pressure transducer generating a signal indicative of the monitored pressure for controlling various aspects of system operation. For example, the pressure signal indicates whether the system is operating within a required pressure range for analysis since the system is designed to operate between maximum and minimum pressure limits. Pressures in excess of the maximum can cause permanent damage to the system structure. Pressures below minimum pressures are associated with undesirably low flow rates through the column. In addition, departures design system pressure may indicate pump and system disfunction such as a clogged column or flow line, a flow leak, or a depleted solvent reservoir. Thus, pressure signal levels outside of the predetermined operating pressure range indicate unsafe or incorrect system operation, requiring corrective action.

In the identified systems, the signal representing measured system pressure signal is also employed to control pump operation through an electronic feedback loop. The described electronic circuit automatically compensates for changes in fluid compressibility, wear of seals and valves, and solvent gas emission. Compensation is detained by change in pump speed corresponding to in measured pressure.

Prior art systems have performed well and have found wide commercial acceptance. However, it has been found that changes in temperature and ofther system operating parameters can cause inaccurate measurement of system pressure. For example, monitoring of pump pressure using a pressure transducer, it has been found that the transducer signal varies with temperature and can drift over time. Such temperature variance and drift creates baseline error relative to the reference level of the pressure signal.

Previously, manual adjustments have been used to correct baseline error as described above. Typically, the system pressure is reduced to zero and any offset or deviation found in the zero pressure measurement is compensated by manual adjustment of a measurement device. This is an unsatisfactory arrangement since its implementation requires ceasing operation of the HPLC system and depressurization of the system. This eliminates the possibility of concurrent manual adjustment in system pressure adjustment. Frequent adjustments can require continued system shut-downs. Furthermore operator attention is diverted from other tasks.

SUMMARY OF THE INVENTION

The present invention resides in an improved system for correcting pressure baseline errors in a fluid pumping system without the drawbacks of the prior art. The present arrangement is simple and straightforward in implementation, reliable in operation, and is achieved in a commercially practical form particularly adapted for, but not limited to, use with HPLC systems.

To the foregoing ends, the present invention is embodied in a system comprising fluid pump means having a piston movable within a chamber for delivering pressurized fluid from the chamber together with pressure measuring means for measuring fluid pressure in the chamber and generating a pressure signal indicative thereof. In this environment the present invention contemplates means for comparing the value of the pressure signal for a selected interval of piston movement to a reference value thereof (e.g. zero) and generating an error signal based on any difference between measured and reference pressure values. The invention further contemplates means for summing the error signal with the pressure signal in a subsequent interval of piston movement to thereby derive an offset corrected pressure output signal for the subsequent interval.

DESCRIPTION OF THE PREFERRED EMBODIMENT

Figure 1:
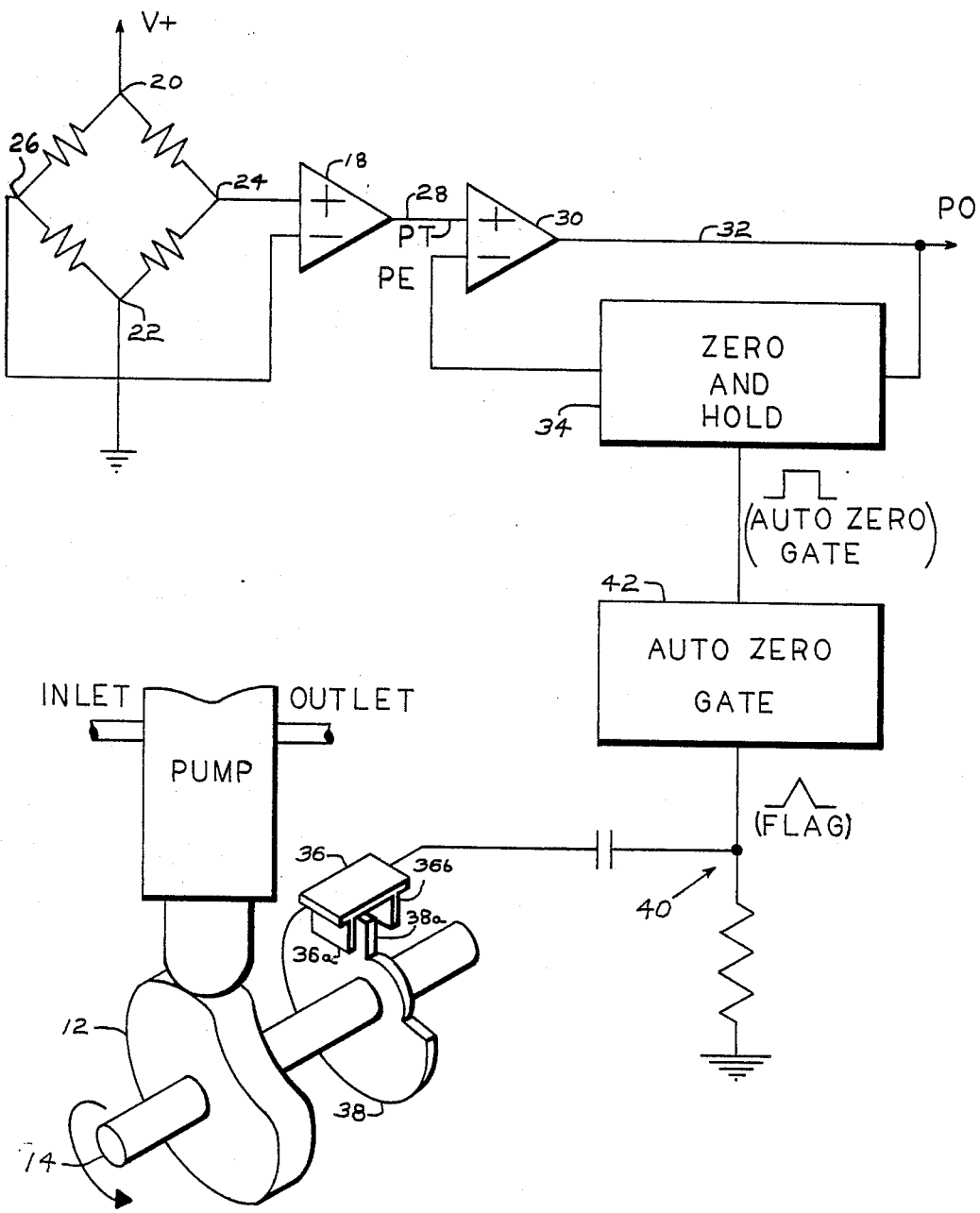
FIG. 1 is a combined schematic and block diagram of the pressure measuring system of the invention. The figure pictorally illustrates the operative interconnection of the pump drive cam and shaft with circuit elements of the system.

As shown in the drawings for purposes of illustration, and particularly FIG. 1 thereof, the present invention is embodied in a pressure measuring system 10 particularly adapted for measuring pressure within the liquid head or pumping chamber of a fluid pump, such as the liquid chromatography pumps exemplified in U.S. Pat. Nos. 4,131,393 and 4,180,375. Reference should be made to these patents for details regarding the structure of such pumps and their manner of use in HPLC applications.

In general, a HPLC pump comprises a piston movable within a piston chamber for drawing fluid into the chamber during a filling interval, pressurizing the fluid during a pressurizing interval, and delivering the pressurized fluid from the chamber during a delivery interval. The pump piston (not shown) is engaged and driven by a cam 12 itself supported for rotation with a stepper motor driven output shaft 14. With this arrangement each 360° rotation of cam 12 drives the pump piston through one operational cycle comprising successive filling, pressurizing and delivery intervals.

Figure 2:
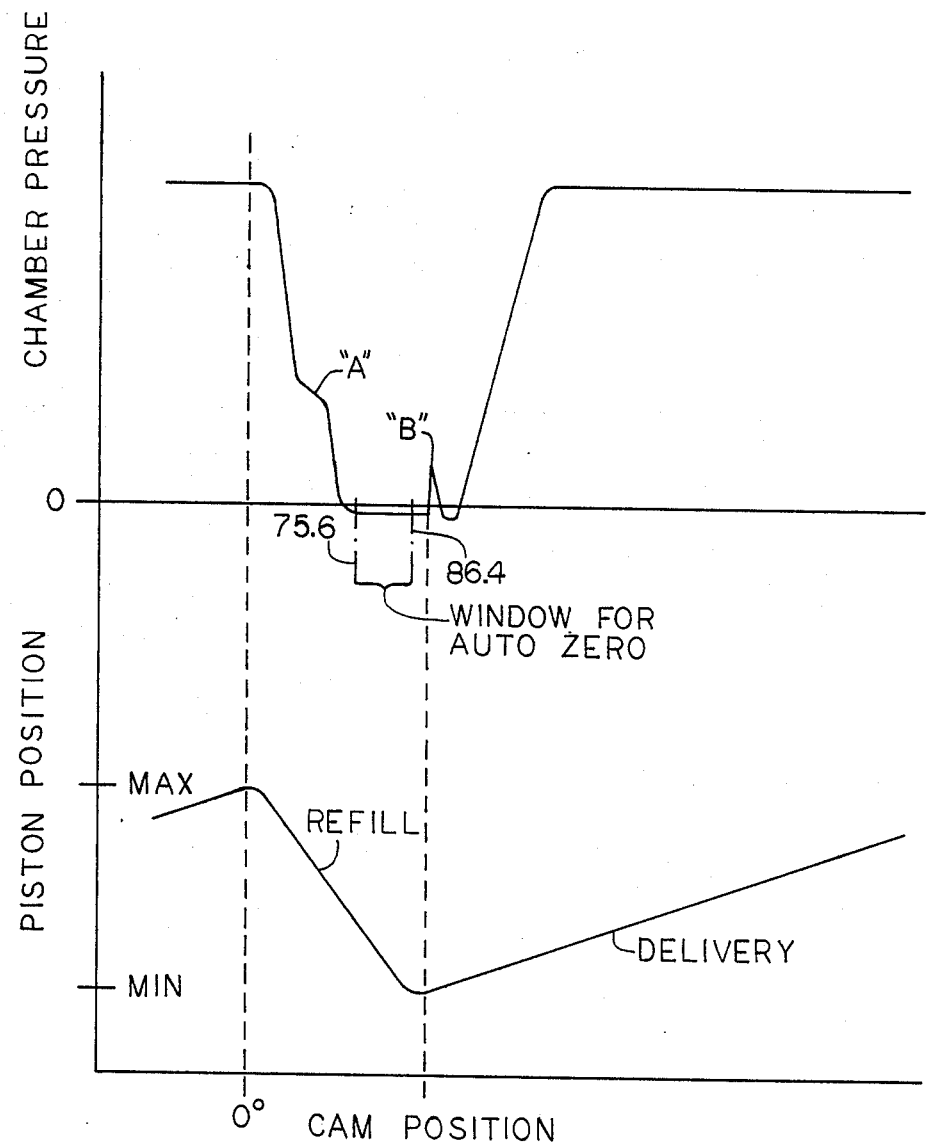
FIG. 2 graphically illustrates a first curve of pump chamber pressure (psi) vs. relative rotational position of the pump drive cam (degrees) and a second curve of piston position vs. the same relative cam position. The first curve depicts chamber pressure at an essentially zero value during a limited interval of pump piston movement during refilling of the pump chamber. The limited interval is defined between rotational cam positions of 75.6° and 86.4°.

FIG. 2 graphically depicts piston chamber pressure and piston position, both as a function of cam rotational position. The zero degree cam position is defined to correspond to the piston position providing maximum compression. Rotation of cam 12 from the zero position drives the piston through the fill interval in which interval the chamber pressure decreases as illustrated. It has been discovered that during the narrow interval illustrated between 75.6° and 86.4° chamber pressure is essentially zero (in fact is slightly though negligibly negative) and free of disturbances. At the end of the fill interval the direction of piston movement reverses thereby increasing chamber pressure, as illustrated, during the pressurizing interval. After a given pressure level is attained, continued movement of the piston operates to discharge or deliver fluid at pressure from the pump during the delivery interval. At the conclusion of the delivery interval, cam 12 will have returned to the zero degree position. In typical pump operation cam 12 rotates at an average rate of 0.1 to 100 revolutions or cycles per minute corresponding to flow rates of 0.01 to 10.0 ml/min.

The details "A" and "B" in the pressure vs. cam position graph, exaggerated for illustrative purposes, are believed to result respectively from backlash in the drive mechanism and inertial fluid flow in the low pressure line.

Referring again to FIG. 1, the present system includes means for measuring pump chamber pressure in the form of a pressure sensitive resistor bridge strain gauge 16 and a cooperating differential amplifier 18. The bridge includes a pair of input terminals 20 and 22 connected to a voltage source V+ and to ground, respectively, and a pair of output terminals 24 and 26 connected to respective non-inverting and inverting inputs of differential amplifier 18. The bridge is secured to a deflectable diaphragm communicating with the pump chamber. The diaphragm is deflectable in varying degrees dependent upon the chamber pressure. In this manner, deflection of the diaphragm correspondingly deflects or strains one or more of the resistive legs of the strain gauge 16 changing the electrical resistance thereof.

When the bridge resistivity is balanced with zero pressure applied to the diaphragm, the bridge output signal across terminals 24 and 26 is zero and hence amplifier 18 supplies a zero level transducer pressure signal $P_T$ at its output 28. As chamber pressure increases, deflection of the supporting diaphragm unbalances the bridge resistivity thereby developing an electrical signal across terminals 24 and 26 indicative of chamber pressure. Differential amplifier 18 thereby supplies a corresponding pressure signal $P_T$ at its output 28 indicative of chamber pressure.

As indicated previously, it has been discovered that changes in temperature or system operational parameters may cause differences between the measured pressure and the actual pressure of the system. For example, the pressure transducer output may vary with temperature or drift over time. In effect, such temperature variance drift creates an offset error in all pressure measurements.

In accordance with the present invention, transducer pressure signal $P_T$ is operated upon to derive an offset corrected pressure output signal $P_O$ on line 32. To this end, the present invention includes summing means in the form of a differential amplifier 30 receiving at one input (i.e. the non-inverting input) the transducer signal $P_T$ from amplifier 18 and supplying at its outut 32 the pressure output signal $P_O$. The invention further includes a zero and hold circuit 34 connected in a feedback path between amplifier output 32 and the second input (i.e. the inverting input) to amplifier 30 circuit 34 measures the pressure output signal $P_O$ during an interval of piston movement when chamber pressure is essentially zero. Any deviation of the pressure signal from a zero value is determined to derive a measure of the offset error in the pressure signal. An error signal $P_E$ is generated and summed with the transducer pressure signal $P_T$ during a subsequent interval of piston movement to derive a corrected pressure output signal $P_O$ for the subsequent pump cycle. In this regard, during the limited interval of zero chamber pressure (75.6° to 86.4°), the zero and hold circuit 34 measures the deviation of the pressure output signal $P_O$ from zero and supplies a feedback error signal $P_E$ to the second input of amplifier 30. In effect, the error signal $P_E$ is summed with the transducer signal $P_T$ causing amplifier 30 to supply an zero level pressure outut signal $P_O$ at 32 during the interval of zero chamber pressure. After the output signal $P_O$ is zeroed, the zero and hold circuitry 34 disregards $P_O$ and any changes therein while continuing to apply error signal $P_E$ to the second input of amplifier 30.

The zero and hold circuit 34 responds to an autozero pulse (FIG. 1) which defines the 75.6° and 86.4° boundaries of the zero pressure interval. The means for generating the autozero pulse comprises an optical signal generator 36, R-C differentiator network 40, and an autozero gate circuit 42.

Signal generator 36 and shutter 38 cooperate to establish the zero degree position of drive cam 12. Generator 36 includes a light source and a light sensor respectively 36a and 36b as illustrated, and is arranged such that a portion of the shutter 38 intercepts the light path therebetween. The shutter, in turn, includes a cutout having one edge 38a which, in the position illustrated, establishes the zero position. When the cutout blocks the light path (as edge 38a passes through the light path) an output signal is generated by the detector. This signal is then differentiated by RC network 40 and is coupled as a control signal (termed a flag) to the autozero gate circuit 42.

Figure 3:
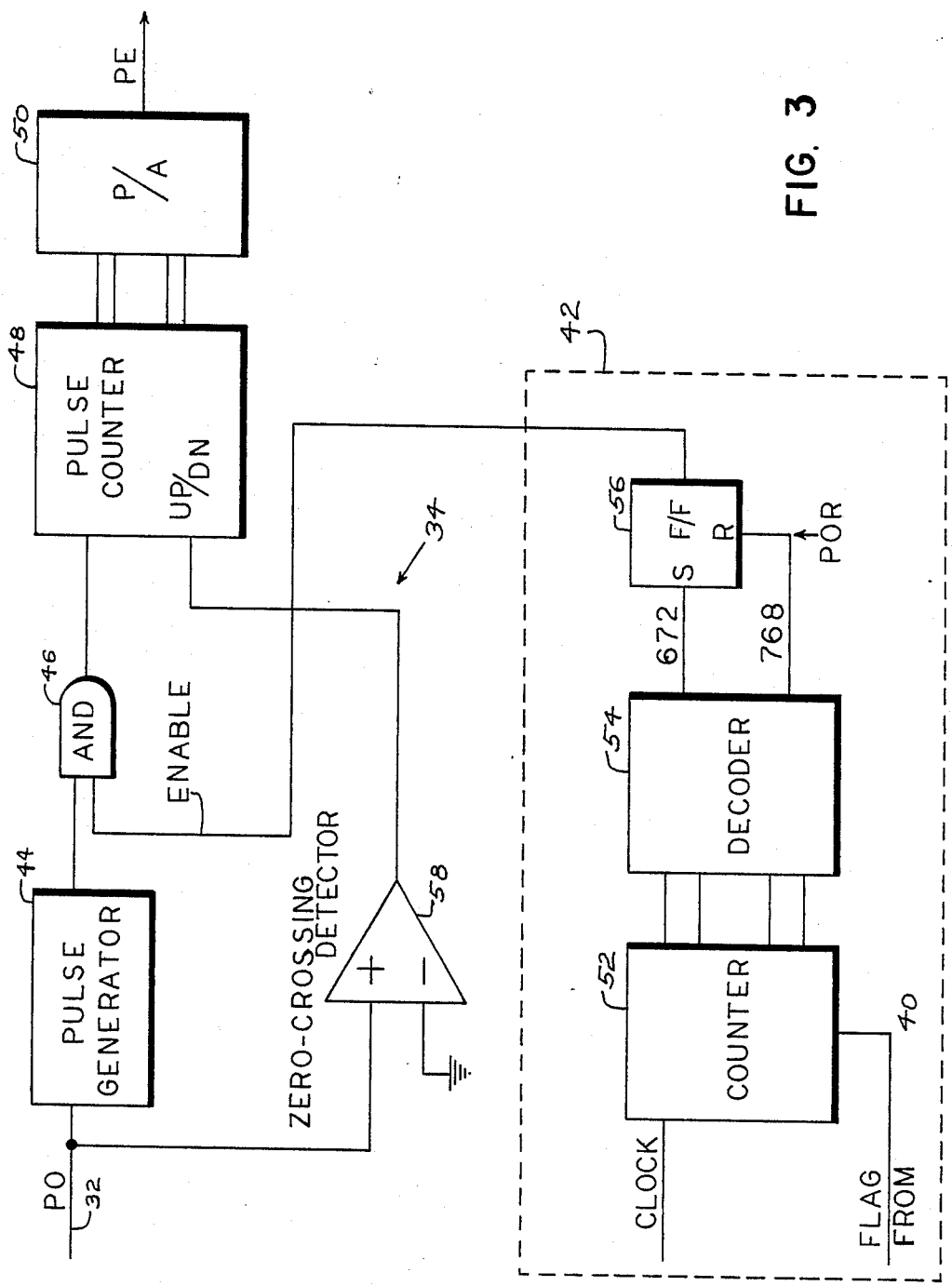
FIG. 3 is a block diagram of the zero and hold circuitry and the auto-zero gate circuitry of FIG. 2.

FIG. 3 illustrates aspects of the foregoing circuitry. In this regard, the zero and hold circuit 34 comprises a voltage controlled pulse generator 44, an AND gate 46, an up/down counter 48, a zero crossing detector 58 and a digital-to-analog converter 50. The frequency of pulse generator 44 is proportional to the magnitude (the polarity is disregarded) of the pressure output signal $P_O$ received from output terminal 32. The pulse generator output is coupled to one input of AND gate 46 such that when the second input of the gate is enabled, the pulses are passed by the gate to the input of up/down pulse counter 48. The counter 48 also receives a logic level signal 47 indicative of the polarity of the pressure output signal at its up/down control input. This logic level signal 47 is derived from the pressure output signal $P_O$ by zero crossing detector 58. The counter 48 is thus directed to count up for a positive pressure error signal $P_O$ and to count down for a negative pressure error signal.

The output of counter 48 is, in turn, converted by D-A converter 50 to the analog error signal $P_E$ supplied to the second input of differential amplifier 30 (FIG. 1). Thus, for a positive pressure error, a positive error signal $P_E$ is developed which, when applied to the inverting or negative input of differential amplifier 30, causes the output pressure signal $P_O$ at terminal 32 to decrease, i.e. be less positive. Conversely, a negative error signal $P_E$ causes the output pressure signal to increase, i.e. be less negative.

Referring again to FIG. 3, autozero gate circuit 42 enables AND gate 46 during the autozero window. Autozero gate circuit 42 includes a counter 52, a decoder 54 and a flip-flop 56. Counter 52 receives the pulse output of a system clock (which clock also drives the stepper motor coupled to shaft 12 illustrated in FIG. 1). The counter reset terminal R receives a flag input from RC network 40. In this manner, when the zero cam position is reached, the flag pulse generated by optical signal generator 36 and RC network 40 resets counter 52 to zero such that the counter begins counting from such zero count at the zero cam position. Counter 52 3200 counts or steps in one 360° revolution of the cam 12.

Decoder 54 coupled to counter 52, has first and second decoder output lines coupled, respectively, to set and reset inputs S and R, respectively, of flip-flop 56. The decoder is configured to supply an output pulse to the set input S at a count of 672 and to supply an output pulse to the reset input R at a count of 768. These two pulses correspond to the respective 75.6 and 86.4 boundaries of the auto zero window. The 672 set input sets the flip-flop which supplies an enable signal to AND gate 46. The AND gate is thus enabled to pass the signal from pulse generator 44 until the 768 pulse output resets the flip-flop removing the enable output from gate 46.

In operation, the zero error signal $P_E$ is developed during the auto zero window the filling interval of each pump cycle and summed with the pressure signal $P_T$ from transducer 16 during subsequent pressurizing and delivery intervals of the cycle. This is achieved by enabling auto-zero gate 42 (FIG. 1) only during the auto zero window between 75.6° and 86.4°. When gate 42 is enabled, the pressure output signal $P_O$ at output terminal 32 is interpreted to derive an error signal $P_E$. The derived zero error signal $P_E$ is continuously applied thereafter to the inverting or negative input of differential amplifier 30. During the autozero window period, when pump chamber pressure is essentially zero, the error signal $P_E$ tends to drive the pressure output signal $P_O$ to a zero value. At other times the error signal $P_L$ serves to cancel any offsets that would otherwise be produced by temperature variance component drift. As a result, an pressure signal $P_O$ having a corrected voltage level at output 32 during succeeding pressurizing and delivery intervals of the pump cycle, which signal follows the chamber pressure as measured by strain gauge 16. Zeroing of the pressure signal $P_O$ is thus effected automatically for each cycle of pump operation without operator intervention and without the need to depressurize the system to make manual adjustments. Moreover, while a preferred embodiment of the invention has been illustrated and described, modifications may be made therein without departing from the invention as defined by the following claims.

What is claimed is:

1. A fluid pump system comprising:
   fluid pump means including a chamber into which a fluid is drawn, in which said fluid is pressurized, and from which said fluid is delivered, during respective filling, pressurizing and delivery intervals of a cycle of said pump means;
   means for measuring the pressure of fluid in said chamber and generating a pressure signal indicative thereof;
   means for generating an error signal during a portion of the chamber fill interval when pressure in said chamber is zero or less than zero, indicating error in zero pressure measurement by said pressure measuring means; and
   means for summing the error signal generated with the measured pressure signal to derive a corrected pressure output signal for use with said fluid pump system.

2. The pump system of claim 1 wherein the pressure measuring means comprises a pressure transducer directly communicating with said pump means chamber.

3. The pump system of claim 1 wherein the error signal generating means includes a zero and hold circuit having an input receiving the measured pressure signal and an output supplying the generated error signal, and gating means responsive to said pump means intervals enabling the zero and hold circuit to process said input signal to generate said error signal during a period when said pump means chamber pressure is zero, or less than zero, and to continually produce the error signal generator at other times disregarding the measured pressure signal.

* * * * *